United States Patent [19]

Wisotsky

[11] 4,235,786

[45] Nov. 25, 1980

[54] PROCESS FOR PRODUCING OIL-SOLUBLE DERIVATIVES OF UNSATURATED $C_4$-$C_{10}$ DICARBOXYLIC ACID MATERIALS

[75] Inventor: Max J. Wisotsky, Highland Park, N.J.

[73] Assignee: Exxon Research & Engineering Co., Florham Park, N.J.

[21] Appl. No.: 80,939

[22] Filed: Oct. 1, 1979

Related U.S. Application Data

[63] Continuation-in-part of Ser. No. 967,276, Dec. 7, 1978, abandoned.

[51] Int. Cl.³ ............................................. C07D 307/60
[52] U.S. Cl. ................................. 260/346.74; 560/203; 562/595
[58] Field of Search ................... 260/346.74; 560/203; 562/595

[56] References Cited

U.S. PATENT DOCUMENTS 3,819,660  6/1974  Cahill et al. ..................... 260/346.74

4,086,251  4/1978  Cengel et al. ................... 260/346.74

FOREIGN PATENT DOCUMENTS

F 10267  9/1956  Fed. Rep. of Germany .
1337724  11/1973  United Kingdom .

Primary Examiner—Henry R. Jiles
Assistant Examiner—Bernard Dentz
Attorney, Agent, or Firm—John J. Mahon

[57] ABSTRACT

An improved process for preparing oil-soluble derivatives of unsaturated $C_4$-$C_{10}$ dicarboxylic acid materials, e.g. the product of the reaction of polyisobutylene and maleic anhydride, under Ene reaction conditions characterized in that said Ene reaction is conducted under acidic conditions as by conducting said reaction in the presence of from 0.01 to 5 wt. %, based on total weight of the reactants, of an oil-soluble strong organic acid containing a hydrogen dissociating moiety which has a pK of less than about 4.0, as exemplified by a $C_{15}$ to $C_{76}$ hydrocarbyl-substituted sulfonic acid, whereby sediment resulting from said Ene reaction is markedly reduced to less than 1 wt. %.

12 Claims, No Drawings

PROCESS FOR PRODUCING OIL-SOLUBLE DERIVATIVES OF UNSATURATED $C_4$-$C_{10}$ DICARBOXYLIC ACID MATERIALS

CROSS-REFERENCE TO RELATED APPLICATION

This application is a continuation-in-part of Ser. No. 967,276, filed Dec. 7, 1978 now abandoned.

BACKGROUND OF THE INVENTION

1. Field of the Invention

This invention relates to high temperature process, i.e. an "Ene" process, for producing oil-soluble derivatives of a monoethylenically unsaturated $C_4$-$C_{10}$ dicarboxylic acid material under conditions of reduced sediment formation as well as to the resulting substantially sediment-free product useful for preparing ashless dispersants utilized in lubricating oil and fuel compositions. In particular, this invention is directed to a sediment-free process involving the "Ene" reaction of a polyolefin and maleic anhydride to provide a precursor for the production of lubricating oil and fuel additives wherein said reaction is carried out in the presence of a sediment-preventing amount of an oil-soluble strong organic acid.

2. Description of the Prior Art

During the past several decades, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. Most commercial ashless dispersants fall into several general categories.

In one category, an amine or polyamine is attached to a long-chain hydrocarbon polymer (the oil-solubilizing portion of the molecule), usually polyisobutylene, through an acid group, such as a dicarboxylic acid material, e.g. succinic anhydride, by forming amide or imide linkages.

In a second category, an alkanol or polyol is attached to said long-chain hydrocarbon polymer through said acid by forming an ester linkage.

In yet another category, the reacton products of hydrocarbon-substituted succinic anhydride, e.g. polyisobutenylsuccinic anhydride, with compounds containing both an amine group and a hydroxy group have been suggested as useful or investigated in the prior art.

The common reactant in all said categories is the long-chain hydrocarbon polymer attached to a dicarboxylic acid group. The polyolefin diacid is readily obtained via the dehydrohalogenation, Diels-Alder or "Ene" reaction of an olefin or a chlorinated olefin with an unsaturated $C_4$ to $C_{10}$ dicarboxylic acid, anhydride or ester thereof, such as fumaric acid, itaconic acid, maleic acid, maleic anhydride, dimethyl fumarate, etc. The dicarboxylic acid material formed via the Ene reaction of an olefin with maleic anhydride results in an alkenyl-substituted anhydride which may contain a single alkenyl radical or a mixture of alkenyl radicals variously bonded to the cyclic succinic anhydride group. This "Ene" product is a preferred precursor for said ashless dispersants since it does not contain any halogen which could be a source of undesired activity when said dispersant is incorporated into the lubricant or fuel.

Unfortunately, the "Ene" reaction of an olefin and maleic anhydride is difficultly reactable and/or results in extensive sediment formation believed to be primarily poly(maleic anhydride) and decomposition products of maleic anhydride.

The deleterious effect of metal ion and alkyl amine contamination upon molten maleic anhydride has been reported, by Vogler et al in the "Journal of Chemical and Engineering Date", Vol. 8, No. 4, pgs. 620–623 of October 1963 entitled "Effect of Contaminants on the Thermal Stability of Maleic Anhydride", to include heat and gas evolution and a solid polymeric material. The structure of poly(maleic anhydride) was the subject of a paper by R. Bacskai, which appeared in the "Journal of Polymer Science", Vol. 14, 1797–1806 (1976) and which teaches that polymerization can be initiated with free radical catalysts and results in the evolution of $CO_2$. The "Ene" reaction of olefins having from 12 to 18 carbons with maleic anhydride to prepare alkenyl succinic anhydride has been conducted in the presence of inorganic acids, anhydrides and salts thereof such as boron phosphate (see German Patent Application No. F 10267 IV b/12 published Sept. 6, 1956).

Another "Ene" reaction of olefins having 6 to 24 carbons with maleic anhydride to prepare said alkenyl succinic anhydrides is carried out in the presence of phosphorous containing sequestrants and hydroxy aromatic compounds for the preparation of detergents of improved color, i.e. reduced colored polymeric by-products.

The suppression of polymeric byproducts arising out of the Ene preparation of alkenyl succinic anhydrides is reported in U.S. Pat. No. 3,819,660 to be achieved by the presence in the reactor of a $C_1$ to $C_3$ alkyl-substituted benzene sulfonic acid (preferably as a solute in acetic anhydride) and in U.S. Pat. No. 4,086,251 by the presence in the reactor of a halogen-containing additive.

Thus, the prior are teaches the "Ene" preparation of alkenyl succinic anhydrides but unfortunately with excessive sediment formation, which sediment appears to be at least in part deleterious poly(maleic anhydride). Further, some of catalysis scavengers and sequestrants which are used in the preparation of alkenyl succinic anhydrides are detrimental for lubricating oil applications in that solid materials are corrosive and/or are oil-insoluble thus contributing to haze and/or sediment.

It is therefore an object of this invention to produce alkenyl succinic anhydrides by the Ene process with reduced sediment formation through the influence of a lubricating oil-soluble material.

SUMMARY OF THE INVENTION

It has been discovered that sediment formation in the "Ene" reaction of an olefin with maleic anhydride can be markedly reduced by the presence of a sediment-reducing amount of an oil-soluble strong organic acid.

Thus the sediment formation problem of said prior art "Ene" processes can be overcome by incorporating into said process environment a sediment-reducing amount e.g. 0.01 to 5 wt.% of an oil-soluble strong organic acid, said acid containing a hydrogen dissociating moiety which has a pK of from $-10$ to $+4$, preferably ranging from about $-3$ to $+2$ based upon the dissociation of the acid in water.

This invention caan be characterized then as a process for the preparation of a hydrocarbon-soluble $C_{30}$-$C_{700}$ hydrocarbyl substituted $C_4$-$C_{10}$ dicarboxylic acid material, preferably $C_{50}$–$C_{120}$ olefin substituted succinic anhydride, comprising the step of reacting said olefin with said dicarboxylic acid material, for example polyisobutylene with maleic anhydride, in a mole ratio of 0.5 to 3, preferably 1 to 2, of olefin to dicarboxylic acid material in the presence of a sediment-reducing amount, generally from 0.01 to 5, preferably 0.05 to 2.5, wt.%, of an oil-soluble strong organic acid, preferably a $C_{15}$–$C_{70}$ optimally $C_{28}$–$C_{36}$ hydrocarbyl substituted sulfonic acid, said wt.% based upon the total weight of the reactants. The reaction temperature ranges from about 150–260, preferably 195°–235° C. for a period of from 1–24 hours, preferably 2–14 hours, optimally from 8–10 hours and under a pressure ranging from atmospheric to an elevated pressure of 500 kpa.

The result of carrying out the process of the invention is that one obtains a reaction product having a materially reduced sediment content. In addition, a reduced reaction time is obtained since it is possible to go to higher reaction temperatures. It is essential to use the oil-soluble strong organic acids: since they are soluble in the olefin reactant which in turn results in a uniform distribution of the acids throughout the reactor and thus avoids localized sediment formation arising out of maldistribution of the organic acid; and, also soluble in the lubricating oil composition even though derivatized along with the alkenyl succinic anhydride during the latter's subsequent derivatization, e.g. reaction with an alkylene polyamine to provide an alkenyl succinimide. It appears that utilization of an oil-soluble organic acid with a pK of less than about 4.0 prevents the sediment formation which is primarily poly(maleic anhydride) either through the mechanism of maintaining the acid pH during the reaction mixture and/or deactivation of metallic ions such as sodium or similar metallic ions which are reported to provoke formation of the poly(maleic anhydride).

DETAILED DESCRIPTION OF THE INVENTION

The product of the inventive process as indicated above is a hydrocarbon-substituted dicarboxylic acid material conventionally considered usually as an olefin diacid. The hydrocarbon substituent chain length generally determines the hydrocarbon solubility of the resulting diacid and the dispersants made therefrom. It is for this reason that we are concerned in this invention with the preparation of diacids having hydrocarbon substitutents ranging from 30–700 carbon atoms, more usually from 36–170. The hydrocarbon substituent can be considered substantially saturated.

The substantially saturated hydrocarbyl substituted diacid material includes diacids, estes and anhydrides as well as imides and amides serived from ammonia or a lower primary amine and also mixtures of such compounds.

In general, these hydrocarbyl substituted dicarboxylic acid materials, preferably alkenylsuccinic anhydrides, and their preparation are well known in the art, for example, see U.S. Pat. Nos. 3,219,666; 3,172,892; 3,272,746; as well as being commercially available, e.g., polyisobutenyl succinic anhydride.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor amount of the copolymer monomers, e.g., 1 to 20 mole % is a $C_4$ to $C_{18}$ nonconjugated diolefin, e.g., a copolymer of isobutylene and butadiene; or a copolymer of ethylene, propylene and 1,4-hexadiene; etc. The olefin polymers may contain cycloalkyl and aromatic groups.

The olefin polymers providing the oil-solubilizing groups will usually have number average molecular weights ($\overline{M}_n$s) ranging from 400 to 10,000 or from about 30 to about 700 carbons, more usually 500 to 2400 or about 36 to 170 carbons, preferably 700 to 1700 or about 50 to 120 carbons, optimally 800 to 1600 or about 60 to 110 carbons with approximately one terminal double bond per polymer chain. An especially valuable starting material for a highly potent dispersant additive are polyalkenes, e.g., polyisobutylene, having about 70 carbons.

The polycarboxylic acid anhydrides are obtained by dehydrating the corresponding acids. Dehydration is readily accomplished by heating the acid to a temperature above about 70° C., preferably in the presence of a dehydration agent, e.g. $P_2O_5$. Cyclic anhydrides are usually obtained from polycarboxylic acids having the acid radicals separated by no more than three carbon atoms, such as substituted succinic or glutaric acids, whereas linear polymeric anhydrides are obtained from polycarboxylic acids having the acid radicals separated by four or more carbon atoms.

The process of the invention, which may be conducted in batch, staged or continuous reactors, is preferably run in a pressure vessel wherein said olefin is first introduced and thereafter the acid material introduced in a staged manner into a melt of said olefin to which has first been added the desired amount of oil-soluble organic acid. The reactants are continually stirred. It is convenient to introduce the oil-soluble organic acid as a solution of acid and oil which facilitates its distribution through the heated liquid alpha-olefin.

Suitable times of reaction will generally be in the range from 1 to 24 hours, temperatures will usually be in the range of 150° C. to 260° C., preferably 190° C. to 250° C., most preferably 195° C. to 235° C. and pressures from atmospheric to 50 psig are generally used. Acid feed to the reactor per 100 parts by weight of olefin may be in the range of: 4 to 30, preferably 6 to 15 parts by weight, preferably added in a staged manner involving from 20 to 50, % of the total acid charge with each stage normally uniformly distributed over the reaction time. A sediment-reducing amount of oil-soluble acid has been found to be at least 0.01, preferably 0.05 to 2.5, optimally 0.1 to 1.0, wt.% (based on the total weight of the reactant charge).

Any oil-soluble strong organic acid can be used in accordance with this invention, said acid containing a hydrogen dissociating moiety which has a pK of −10 to about +4.0, preferably from about −3 to about +2. The term pK for the purpose of this disclosure is used herein to express the aqueous dissociation of the acid used to inhibit the sediment formation which is provoked by thermal and/or cationic catalysis of the polymerization of the polycarboxylic acid material under "Ene" reaction conditions. Thus, pK can be defined as the negative logarithm to the base 10 of the equilibrium constant for the dissociation of the oil-soluble organic acid. For the purposes of this invention, the strong acids have a pK of up to about 4.0 and optimally ranges from about −3 to about +2 whereas the weak acid which fails to inhibit sediment formation has an acid moiety providing a pK of more than about 4.8, usually in the range of 5 to 8 and can be represented by stearic acid.

As used herein, oil-soluble is defined as those organic acids which themselves are substantially soluble in mineral oil at 20° C. to at least 50 wt.%.

Representative classes of the oil-soluble strong organic acids are represented by maleic acid, malonic acid, phosphoric acid, thiophosphoric acids, phosphonic acid, thiophosphonic acids, phosphinic acid, thiophosphinic acids, sulfonic acid, sulfuric acid, and alpha-substituted or nitrilocarboxylic acids wherein the oil-solubilizing group or groups are hydrocarbyl and containing from 15 to 76, preferably from 24 to 40, optimally 28 to 36, total carbon atoms.

Particularly preferred for use in this invention for inhibiting sediment formation are the oil-soluble sulfonic acids which are typically alkaryl sulfonic acids. These sulfonic acids are typically obtained by the sulfonation of alkyl substituted aromatic hydrocarbons such as those obtained from the fractionation of petroleum by distillation and/or extraction or by the alkylation of aromatic hydrocarbons as, for example, those obtained by alkylating benzene, toluene, xylene, naphthalene, diphenyl and the halogen derivatives such as chlorobenzene, chlorotoluene and chloronaphthalene. The alkylation may be carried out in the presence of a catalyst with alkylating agents having from 9 to about 70 carbon atoms such as, for example, haloparaffins, olefins that may be obtained by dehydrogenation of paraffins, polyolefins as, for example, polymers from ethylene, propylene, etc. Preferred sulfonic acids are those obtained by the sulfonation of hydrocarbons prepared by the alkylation of benzene or toluene with tri-, tetra- or pentapropylene fractions obtained by the polymerization of propylene. The alkaryl sulfonic acids contain from 9 to 70, preferably from 18 to 34, optimally from 22 to 30, carbon atoms per alkyl substituent(s) in the aryl moiety as illustrated by the formula

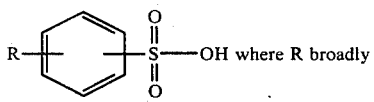

where R broadly contains from 9 to 70 carbons, etc. Particularly preferred is an alkylated benzene sulfonic acid having a molecular weight ($\overline{M}_n$) of from 475 to 600 and an average of 2 alkyl groups wherein each of said groups contain an average of 11 to 15 carbons.

The alkylated benzene from which the sulfonic acid is prepared is obtained by known alkylation processes; benzene being generally reacted with such alkylating agents as isobutylene, isoamylene, diisobutylene, triisobutylene, etc., or olefin-containing mixtures containing from refinery gases. Boron trifluoride is a preferred alkylating agent.

Among the $C_9$–$C_{70}$ alkylated benzenes which are preferably employed in the preparation of the sulfonic acid are p-isopropylbenzene, p-amylbenzene, isohexylbenzene, p-octylbenzene, nonylbenzene, ditertiaryoctylbenzene, waxy alkylated benzenes, benzenes alkylated with suitable branched chain polymers of up to 70 carbons obtained from propylene, butylene, amylene or mixtures thereof or the like. Optimally, nonyl or dodecyl or either of their equivalents in a mixture of alkyls is employed in preparation of the sulfonic acid.

The oil-soluble phosphorous-containing acids can be represented by the following general formulae:

| | |
|---|---|
| (1) R'ZPOZ$_2$H | phosphoric or thiophoshoric |
| (2) (R'Z)PZ$_2$H | acids, |
| (3) (R')$_2$PZ$_2$H | phosphinic or thiophosphinic acids; and, |
| (4) R'POZ$_2$H | phosphonic or thiophosphonic acid | wherein R' is one or two (same or different) $C_9$–$C_{70}$ hydrocarbyl radicals such as alkyl, aryl, alkaryl, aralkyl, and alicyclic radicals to provide the required oil solubility with a total carbon content of 15 to 70 carbons, O is oxygen and Z is oxygen or sulfur. The acids are usually prepared by reacting $P_2O_5$ or $P_2S_5$ with the desired alcohol or thiol to obtain the substituted phosphoric acids. The desired hydroxy or thiol compound should contain hydrocarbyl groups of from about 9 to about 70 carbon atoms with at least 15 total carbon atoms average to provide oil solubility to the product. Examples of suitable compounds are hexyl alcohol, 2-ethylhexyl alcohol, nonyl alcohol, dodecyl alcohol, stearyl alcohol, amylphenol, octylphenol, nonylphenol, methylcyclohexanol, alkylated naphthol, etc., and their corresponding thio analogues; and mixtures of alcohols and/or phenols such as isobutyl alcohol and nonyl alcohol; orthocresol and nonylphenol; etc., and mixtures of their corresponding thio analogues.

In the preparation of the hydrocarbyl substituted thiophosphoric acids, any conventional method can be used, such as, for example, the preparation described in U.S. Pat. No. 2,552,570; 2,579,038 and 2,689,220. By way of illustration, a dialkaryl substituted dithiophosphoric acid is prepared by the reaction of about 2 moles of $P_2S_5$ with about 8 moles of a selected alkylated phenol, e.g. a mixture of $C_8$–$C_{12}$ alkyl substituted phenols, i.e. nonyl phenol, at a temperature of from 50° C. to 125° C. for about 4 hours. In the preparation of hydrocarbyl substituted thiophosphinic acids as conventionally known, a disubstituted phosphine is oxidized to give disubstituted thiophosphinic acids (see F. C. Whitmore's Organic Chemistry published by Dover Publications New York, N.Y. (1961) page 848). A highly useful organo-phosphorous-containing acid is commercially available as Tiger Acid from E. I. duPont and believed to be tridecyl mono/dihydrogen phosphoric acid containing an average of 16 to 26 carbons.

Particularly preferred for preparation of oil-soluble phosphoric, phosphonic and phosphine acids useful in the process of the invention are mixed aliphatic alcohols obtained by the reaction of olefins of carbon monoxide and hydrogen and substituted hydrogenation of the resultant aldehydes which are commonly known as "Oxo" alcohols, which Oxo alcohols for optimum use according to this invention will contain an average of about 13 carbon atoms. Thus for the purposes of this invention a di-$C_{13}$ Oxo phosphoric acid which has an acid dissociating moiety with a pK of about 2.0 is preferred. The oil-soluble phosphorous-containing acids are readily prepared from these alcohols by reaction with $P_2O_5$ as is well known in the art.

Another class of useful sediment-inhibiting agents are oil-soluble hydrocarbyl substituted maleic acids of the general formula

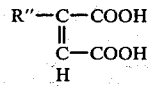

wherein R″ is an oil-solubilizing, hydrocarbyl group containing from 15 to 70 carbons. Representative of these oil-soluble maleic acid derivatives are pentadecylmaleic acid (1,2-dicarboxyl pentadecene-1), hexadecylmaleic acid, eicosylmaleic acid, triacontanylmaleic acid, polymers of $C_2$–$C_5$ monoolefins having from 15 to 70 or more carbons substituted onto said maleic acid, etc.

Additional sediment-inhibiting agents are oil-soluble hydrocarbyl containing from 15 to 70 carbons, substituted malonic acid of the general formula

wherein R″ has the meaning set forth above as an oil-solubilizing hydrocarbyl group which is illustrated by the following representative compounds which include the malonic acid counterparts of the above-referenced hydrocarbyl substituted maleic acids, i.e. pentadecylmalonic acid, hexadecyl malonic acid, etc.

Another class of sediment-inhibiting agents are oil-soluble hydrocarbyl containing from 15 to 70 carbons, substituted sulfuric acids of the general formula R″$HSO_4$ wherein R″ has the meaning set forth above as an oil-solubilizing group which is represented by the following compounds which include pentadecylsulfuric acid; hexadecylsulfuric acid, eicosylsulfuric acid, triacontanylsulfuric acid, etc.

A further group of strong acids which can be used in accordance with the invention to inhibit sediment formation are oil-soluble mono- and di-α-substituted hydrocarbyl carboxylic acids having the general formula:

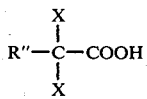

where R″ is a $C_{15}$–$C_{70}$ hydrocarbyl, oil-solubilizing group as referenced above and X refers to hydrogen, nitrilo or nitro group. These materials are represented by the following: α-nitro and α,α-di-nitro, substituted acids such as dodecanoic, pentadecanoic, octadecanoic, docosanoic, octacosanoic, tricontanoic, tetracontanoic, pentacontanoic, hexacontanoic, heptacontanoic, etc.

The following examples illustrate more clearly the process of the present invention. However, these illustrations are not to be interpreted as specific limitations of this invention.

EXAMPLE 1

125 pounds of polyisobutylene having a number of average molecular weight ($\overline{M}_n$) of about 900 (carbon chain lengths of 35 to 100 carbons) and a specific viscosity @ 100° C. of 210 was charged to a 30-gallon glass-lined reactor equipped with a stirrer and adapted to be closed. To this reactor was then added 0.35 pounds of a mineral oil solution containing 50% by weight of an alkylated benzene sulfonic acid having an ($\overline{M}_n$) of 500 and containing an average of about total 30 carbons). The resulting mixture was stirred while heating to 120° C. under a vacuum of about 600 mm. Hg and held at 120° C. for 1 hour. While maintaining at 120° C. and after returning to ambient pressure, 13.2 pounds of maleic anhydride was added and the reaction vessel sealed. The system was heated to 235° C. and with the pressure maintained at about 150 kilo pascals (1.36 atmospheres), kept at 235° C. for 6 hours. The vessel was then opened and the system sparged with $N_2$ at 235° C. for 2 hours.

The resulting product had a kinematic viscosity @ 100° C. of 603.6 centistokes with 0.2% sediment (measured by a test in which 50 ml of heptane and the solution placed in a calibrated tube prior to centrifuging at about 1300 rpm for 20 minutes and thereafter measuring the sediment in said calibrated tube).

EXAMPLE 2

The procedure of Ex. 1 was followed except that no sulfonic acid was present.

The resulting product had a kinematic viscosity @ 100° C. of 397.5 centistokes and 3.0% sediment. It is thus apparent that the presence of about 0.13 wt.% of an acid reduced the sediment formation by 93%.

EXAMPLE 3

In laboratory scale preparations of polyisobutenyl succinic anhydride, a number of acids are hereinafter shown to markedly reduce sediment formation normally formed in the "Ene" reaction of polyisobutylene and maleic anhydride.

In each of the reactions, 250 grams polyisobutylene is reacted with 13.8 grams of maleic anhydride in the presence of 0.1 gram of silicone antifoamant by heating the polyisobutylene to 193°–198° C. under a nitrogen blanket for about 1 hour and then adding the maleic anhydride and antifoamant and as desired acid and thereafter raising the temperature to 230°–235° C. followed by reflux for 4 hours and then cooling with nitrogen stripping.

The results of some of the runs are hereafter set forth in the table and show that oil-soluble strong organic acids reduce the sediment and further confirm the optimum utility of alkylated benzene sulfonic acid containing an average of about 30 total carbons and having a ($\overline{M}_n$) of about 500.

Example 3-D confirms the reported observations (see Vogler et al reported in Description of Prior Art) that the presence of alkali ions such as sodium ($Na^+$) markedly increases sediment formation.

One important use for the oil-soluble alkenylsuccinic anhydride products, those whose alkenyl substituent have ($\overline{M}_n$) in the range of about 400 to 10,000, usually 500 to 2500, is through their alkenyl succinimides of ethylene diamine, diethylene triamine, triethylene tetraamine and tetraethylene pentamine as dispersant additives for lubricating oils. Similarly useful are the polyol esters, preferably pentaerythritol esters, of the oil-soluble alkenylsuccinic anhydrides. Since the sediment-reducing additive of the invention is oil-soluble as well as being soluble in the alkenylsuccinic anhydride, it need not be removed though it must not become oil-insoluble upon derivatization or because of incompatibility with other additive components or contain moieties such as a chloro substituent that would adversely effect the performance of the lubricating oil.

The inorganic acids are disadvantageous since they are not soluble in the reactants making them difficult to distribute uniformly through the reactant mix and generally corrosive to the reactor and environmentally dangerous to contain and dispose of and/or add to the burden of separating the reactor mix from the alkenylsuccinic anhydride product.

The oil-insoluble organic acids add as well to the burden of removing additional material from the product but also present a potential hazing material in the formulated lubricating oil.

The halogen-containing acids, particularly those containing chlorine, are corrosive both to the reactor and to the machine using the lubricating oil formulated with the alkenylsuccinic product or its derivative.

The invention in its broader aspect is not limited to the specific details shown and described and departures may be made from such details without departing from the principles of the invention and without sacrificing its chief advantages.

| Run No. | Polyisobutylene ($\overline{M}n$) | Type | Acid Wt.% | Sediment Resulting Wt.% |
|---|---|---|---|---|
| 3A | 900 | — | 0 | 1.8 |
| 3B | 900 | alkylbenzene sulfonic acid[1] | 0.4 | 0.2 |
| 3C | 900 | alkylbenzene sulfonic acid[1] | 0.1 | 0.4 |
| 3D | 900 | NaHSO$_4$ | 0.3 | 3.0 |
| 3E | 900 | tridecyl mono/diacid phosphate[2] | 0.2 | 0.8 |
| 3G | 1300 | — | 0 | 1.0 |
| 3K | 1300 | alkylbenzene sulfonic acid[1] | 0.2 | 0.08 |
| 3N | 1300 | alkylbenzene sulfonic acid[1] | 0.2 | 0.16 |

[1] an alkylbenzene sulfonic acid having a ($\overline{M}n$) of about 530 and containing an average total carbon content of about 30 carbons.
[2] Tiger Acid sold by the Petroleum Div. of E. I. duPont, Wilmington, Delaware and believed to have at least 16 average carbon content per molecule.

What is claimed is:

1. An improved process for preparing oil-soluble derivatives of a monoethylenically unsaturated $C_4$–$C_{10}$ dicarboxylic acid, anhydride or ester comprising the Ene reaction of said unsaturated $C_4$–$C_{10}$ dicarboxylic acid, anhydride or ester and an olefin containing from 30 to 700 carbons characterized in that said Ene reaction is carried out in the presence of at least a sediment-reducing amount of an oil-soluble, strong organic acid, having a pk less than about 4, and said acid is of the class consisting of hydrocarbyl substituted phosphorous containing acids, hydrocarbyl substituted maleic acids, hydrocarbyl substituted malonic acids, hydrocarbyl substituted sulfuric acids, hydrocarbyl substituted sulfonic acids and hydrocarbyl alpha-substituted carboxylic acids wherein the alpha substituent or substituents is selected from the group consisting of nitrilo or nitro, said hydrocarbyl substituents having at least 15 carbons.

2. An improved process according to claim 1 wherein said olefin is polyisobutylene and said dicarboxylic acid, anhydride or ester is maleic anhydride.

3. An improved process according to claim 1 wherein said acid is an oil-soluble sulfonic acid having a hydrocarbyl substituent containing from 15 to 70 carbons.

4. An improved process according to claim 3 wherein said dicarboxylic acid anhydride is maleic anhydride, said olefin is poly(isobutylene) and said sulfonic acid is present in an amount of from 0.01 to 5 wt.% based on the total weight of said reactants and is an alkaryl sulfonic acid containing from 24 to 40 total carbon atoms per molecule.

5. An improved process according to claim 4 wherein said acid is an alkylated benzene sulfonic acid having a number average molecular weight ranging from 475 to 600.

6. An improved process according to claim 1 wherein the olefin is a $C_2$–$C_5$ monoolefin homopolymer.

7. An improved process according to claim 1 wherein the olefin is a copolymer of two or more $C_2$–$C_5$ monoolefins.

8. An improved process according to claim 1 wherein the olefin is a copolymer of a $C_2$–$C_5$ monoolefin with a minor amount of a $C_4$–$C_{18}$ nonconjugated diolefin.

9. An improved process according to claim 1 wherein the olefin is ethylene.

10. An improved process according to claim 6 wherein the olefin is propylene.

11. An improved process according to claim 6 wherein the olefin is butylene.

12. An improved process according to claim 6 wherein the olefin is pentene.

* * * * *